United States Patent [19]

Urech

[11] 4,061,853
[45] Dec. 6, 1977

[54] VIRTUALLY SOLVENT-FREE CRYSTAL FORM OF THE SODIUM SALT OF CEPHACETRIL

[75] Inventor: Jakob Urech, Basel, Switzerland

[73] Assignee: Ciba-Geigy Corporation, Ardsley, N.Y.

[21] Appl. No.: 737,376

[22] Filed: Nov. 1, 1976

[30] Foreign Application Priority Data

Dec. 9, 1975 Switzerland .................. 15974/75

[51] Int. Cl.$^2$ ............................................. C07D 501/26
[52] U.S. Cl. ...................................... 544/30; 424/246

[58] Field of Search .................................. 260/243 C

[56] References Cited

U.S. PATENT DOCUMENTS 3,483,197  12/1969  Bickel et al. .................... 260/243 C Primary Examiner—Nicholas S. Rizzo
Attorney, Agent, or Firm—John J. Maitner

[57] ABSTRACT

The invention relates to a new, virtually solvent-free crystal form of the sodium salt of Cephacetril and to processes for the manufacture thereof.

9 Claims, No Drawings

VIRTUALLY SOLVENT-FREE CRYSTAL FORM OF THE SODIUM SALT OF CEPHACETRIL

The invention relates to a new crystal form of the sodium salt of Cephacetril, having advantageous properties, and to processes for the manufacture thereof.

The generic name Cephacetril signifies a chemical compound of the formula

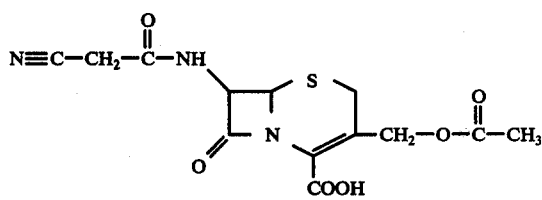

the systematic name of which is 7β-cyanoacetylamino-3-acetoxymethyl-3-cephem-4-carboxylic acid. This compound is a derivative of cephalosporanic acid and is thus also called 7-cyanoacetylamino-cephalosporanic acid.

Cephacetril displays antibiotic activity against numerous Gram-positive and Gram-negative pathogens. Aqueous solutions of the sodium salt of Cephacetril can be used parenterally, such as intravenously or intramuscularly, for example for combating infections of the respiratory tract, urogenital infections, peritonitis, infections of bones and joints, infections of the skin and the tissue of soft parts, bacterial meningitis and bacterial endocarditis. The sodium salt of Cephacetril, which is also known under the trade name "CELOSPOR," is therefore of particular importance.

Cephacetril and processes for the manufacture thereof have been disclosed by Bickel et al., for example in U.S. Pat. No. 3,483,197. The crystal form, known hitherto, of the sodium salt of Cephacetril, is designated as modification A, has the following X-ray powder diagram (taken with a Guinier-de Wolff camera using a Cu:K$_\alpha$ radiation source):

| Interplanar spacings d in Å | Relative line intensities I |
|---|---|
| 12.9 | vst |
| 7.83 | m |
| 7.56 | vw |
| 6.97 | w |
| 6.71 | w |
| 5.64 | vw |
| 5.57 | vw |
| 5.17 | m |
| 5.07 | vw |
| 4.31 | vw |
| 4.24 | m |
| 4.09 | st |
| 3.91 | st |
| 3.82 | w |
| 3.74 | vw |
| 3.63 | m |
| 3.49 | m |
| 3.40 | m |
| 3.34 | vw |
| 3.24 | vw |
| 3.19 | w |
| 3.14 | vw |
| 3.09 | w-m |
| 3.01 | m |

The relative line intensities given in the above table and in the tables which follow are estimated and have the following meanings:

vst = very strong
st = strong
m = medium
w = weak
vw = very weak

Modification A is, for example, obtained when a solution, prepared at about 60°, of Cephacetril in almost anhydrous ethanol, containing less than 1% of water, is cooled to about 30° and a concentrated to saturated solution of a sodium salt of a carboxylic acid, for example of 2-ethylhexanoic acid or acetic acid, in water or in a mixture of water and a water-miscible organic solvent, such as methanol, ethanol, isopropanol, acetone, acetonitrile, dimethylformamide and the like, is added to this supersaturated solution. Modification A, obtained in this way, always contains inclusions of the solvent used, which either cannot be removed at all or can only be removed when the crystal lattice is destroyed. However, such a product, the crystal lattice of which has been destroyed, cannot be stored without the active compound decomposing. For parenteral administration it is only possible to use an active compound which either contains no inclusions of solvent at all or at most contains harmless inclusions of solvent. Thus, virtually the only solvent which can be used is ethanol. The known modification A contains about 4-6% of ethanol of crystallisation which can neither be removed on drying in vacuo at about 50° nor on lyophilising. The ethanol can only be removed at about 100°, but then the disadvantages of decomposition, which have been described above, occur.

A disadvantage of using anhydrous ethanol is that it is difficult to obtain such ethanol in a state completely free from traces of methanol and acetone. However, methanol and acetone are preferentially incorporated in the crystal lattice of modification A and, because of the toxicity of these solvents, this is a disadvantage for parenteral administration.

When stored in moist air, modification A slowly loses ethanol of crystallisation, partial decomposition of the active compound occurring, and this manifests itself by the aqueous solution of the active compound becoming turbid.

The known modification forms matted, acicular crystals which, in this form, are unsuitable for machine-filling into ampoules. The compaction, and subsequent grinding of the active compound, which is normally carried out to solve this problem, cannot be used in the case of modification A, because the latter can only be compacted with decomposition.

Admittedly, it is possible to machine-fill the amorphous lyophilised form which can be prepared from modification A, but this form still contains about 2% of ethanol and, furthermore, is less stable, due to the amorphous character, than a crystallised form.

The previously known physical forms of the sodium salt of Cephacetril also have certain properties which are undesirable in a medicament, since they make it more difficult to manufacture, and to use, pharmaceutical administration forms prepared therefrom. Accordingly, there is a demand for a form which is more suitable for the purposes mentioned.

It has now been found that the sodium salt of Cephacetril can be obtained in a new crystal modification which, in the following text, is designated modification B, contains virtually no inclusions of solvent and which meets, to a far greater extent, the requirements made of a pharmacological active compound with respect to processability and stability, when the sodium salt of Cephacetril is caused to crystallise from an aqueous-ethanolic solution.

The new crystal form of the sodium salt of Cephacetril differs from the known modifications A in that it has a different X-ray powder diagram which, when taken with a Guinier-de Wolff camera using a $Cu:K_\alpha$ radiation source, has the following interplanar spacings and relative line intensities:

| Interplanar spacings d in Å | Relative line intensities I |
|---|---|
| 15.2 | m |
| 10.7 | m |
| 7.86 | m |
| 7.60 | w |
| 7.03 | m |
| 5.04 | m-st |
| 4.94 | w |
| 4.65 | st |
| 4.39 | st |
| 4.10 | vst |
| 4.01 | m |
| 3.66 | m |
| 3.59 | vw |
| 3.50 | st |
| 3.36 | vw |
| 3.30 | m |
| 3.18 | m |
| 3.11 | vw |
| 3.04 | w |
| 3.02 | w |
| 2.96 | w |
| 2.88 | w |

Modification B also forms matted acicular crystals, but these are virtually free from inclusions of solvent of crystallisation. They can be dried down to a negligible residual content of about 0.2 to 0.4% of ethanol and about 0.2 to 0.4% of water, without the crystal lattice being destroyed. Compared with modification A or with the amorphous lyophilised form obtained from modification A or B, modification B guarantees a substantially higher stability of the active compound. The matted needles of a modification B can be converted, by compaction and subsequent grinding of the compacted product, into a form which can be machine-filled, that is to say is free-flowing, without any loss of stability. There is no tendency to absorb water from moist air so that the storage stability is increased even in such surroundings. Because no solvents of crystallisation are incorporated in the modification according to the present invention, there is also no danger of an enrichment of methanol or acetone from the ethanol. A further advantage is that it is not absolutely necessary to lyophilise modification B; instead, it can be processed further after it has been dried in vacuo in the customary manner.

The solution properties of modification B in physiologically acceptable solvents, such as in distilled water or twice distilled water, sterile physiological sodium chloride solution or sterile 5% strength glucose solution, correspond to those of modification A or of the lyophilised form thereof.

Moreover, in the manufacture of modification B, it is possible to work with a higher concentration and this means that, in addition to scope for using smaller, space-saving reaction vessels, solvent is also saved.

Accordingly, the new modification B of the sodium salt of Cephacetril meets, to a substantially greater extent than its previously known physical forms, the requirements, with respect to stability and processability, which the use of this active compound as a medicament must fulfil.

The process for the manufacture of the new crystal form of the sodium salt of Cephacetril, which form is virtually free from solvent and has the X-ray diffraction spectrum indicated above, is characterised in that the sodium salt of Cephacetril is caused to crystallise from a supersaturated, aqueous-ethanolic solution.

The supersaturated, aqueous-ethanolic solution of the sodium salt of Cephacetril can be prepared by dissolving any of the previously known physical forms of this salt, for example the ethanol-containing modification A or the amorphous lyophilised form, or the mixture of such a form with the new modification B or even the pure modification B, at elevated temperature in an ethanol/water mixture, or by dissolving the salt in pure water and subsequently adding ethanol, preferably anhydrous ethanol, to this aqueous solution in the amount which is necessary for supersaturation.

Preferably, the supersaturated aqueous-ethanolic solution of the sodium salt of Cephacetril is prepared in situ by dissolving the free acid of Cephacetril at about 40° to about 60° C, preferably at about 50° to 52° C, in aqueous ethanol, in particular in ethanol which preferably contains about 4 to about 12%, in particular about 8% of water, and adding to this solution, optionally after cooling to, for example, about 30° C, a concentrated aqueous solution, or preferably a concentrated aqueous-ethanolic solution, of a sodium salt of a weak acid.

Modification B already crystallises from the supersaturated solution, thus obtained, of the sodium salt of Cephacetril when about 5% of the calculated amount of the sodium salt of the weak acid have been added. The precipitation can be completed by cooling to 0° to 10° C, in particular to about 0° to 3° C.

Suitable sodium salts of weak acids are those which are readily soluble in water or in aqueous ethanol. Examples which may be mentioned are the sodium salts of organic carboxylic acids, such as lower alkanecarboxylic acids with up to 10, in particular up to 4, carbon atoms, for example the sodium salts of 2-ethyl-hexanoic acid, of butyric acid or of propionic acid, and in particular sodium acetate which can also be employed in the form of its trihydrate. Advantageously, sodium acetate trihydrate is added as an aqueous-ethanolic solution, preferably in a ratio of sodium acetate trihydrate:water:ethanol of 1:1:1 (parts by weight), to the ethanolic solution of Cephacetril.

The sodium salt of Cephacetril is readily soluble in water and sparingly soluble in ethanol. The content of water in the ethanol is thus decisive for the yield. A water content of about 4 to about 12, in particular about 8%, in the supersaturated solution is preferred. If the water content falls below 4%, there is a danger that modification A may be formed.

The temperature has an influence on the solubility of the sodium salt of Cephacetril in the aqueous-ethanolic solvent, the solubility increasing with the temperature. If the temperature is raised too high, decomposition phenomena become increasingly manifest. The choice of temperature at the start of crystallisation, however, also exerts a dominant influence on the crystal form being produced. In order to produce modification B, the preferred temperature of the supersaturated solution is initially about 20° to 30° C, in particular 25° C, in the case of recrystallisation from the aqueous-ethanolic solvent, or in the case of in situ preparation from Cephacetril and the sodium salt of a weak acid, this temperature is about 30° C. When more ethanol is added, or more sodium salt of a weak acid is added, respectively, modification B precipitates and the precipitation can be completed by cooling, preferably to about 0° to about 10° C, for example to about 3° C.

Modification B, which can be manufactured according to the invention, can be freed in vacuo at elevated temperature, at about 40° to 50° C, from adhering ethanol and water, leaving only traces which do not interfere.

After compacting and grinding of the compacted product, a free-flowing powder is obtained which, when working under sterile conditions, can be directly machine-filled in the desired amount, for example into phials or ampoules.

The examples which follow illustrate the production of the new crystal form of the sodium salt at Cephacetril but should not be regarded as limiting the scope of the invention.

EXAMPLE 1

20 g of 7-cyanoacetylamino-cephalosporanic acid are dissolved in 740 ml of ethanol (containing 3.97% of water) which has been warmed to 60° C. The clear colourless solution is filtered and the filter residue is rinsed with 80 ml of ethanol. The filtrate is slowly cooled to 30° C and 18.2 ml of a solution consisting of 66.3 parts by weight of sodium acetate trihydrate in 84 parts by weight of water are then added, whilst stirring. The white suspension is cooled to +10° C. The precipitated crystals of the sodium salt of 7-cyanoacetylamino-cephalosporanic acid are filtered off, washed with twice 50 ml of ethanol at 0° C and are dried overnight at 40° C in a water pump vacuum and subsequently for 24 hours at the same temperature in a high vacuum. Water content: 0.3%; ethanol content: 0.2%; the X-ray diffraction spectrum corresponds to that of modification B.

EXAMPLE 2

20 g of 7-cyanoacetylamino-cephalosporanic acid are dissolved in 280 ml of 92% strength ethanol which has been warmed to 50° C. The solution is filtered and the filter residue is rinsed with 30 ml of 92% strength ethanol. The filtrate is cooled to 30° C and 25.9 ml of a solution consisting of one part by weight of sodium acetate trihydrate, one part by weight of ethanol and one part by weight of water and added, whilst stirring. The mixture is first stirred for a further 2 hours at 20° C and then cooled to 7° C. The crystals of the sodium salt of 7-cyanoacetylamino-cephalosporanic acid are filtered off, rinsed with twice 50 ml of ethanol and dried for 7 hours at room temperature in a water pump vacuum and for 8 hours at 40° C in a high vacuum. Water content: 0.25%; ethanol content: 0.20%. The X-ray diffraction spectrum corresponds to that of modification B.

EXAMPLE 3

15 liters of ethanol with a water content of 8% (weight/volume) are warmed to 50°-52° C in a 20 liter reaction vessel. Under a nitrogen blanket and whilst stirring, 1 kg of 7-cyanoacetylamino-cephalosporanic acid is introduced into the warm ethanol. The acid dissolves in the course of 4-5 minutes to give a completely clear solution. The hot aqueous-ethanolic solution is immediately filtered through a cardboard filter into a second 20 liter reaction vessel and, after rinsing with about 1.2 liters of 92% strength ethanol, the clear filtrate is allowed to cool to 32°-30°. Whilst stirring well, 1.3 liters ($\simeq$ 1.32 kg) of a reagent solution consisting of 0.44 kg each of water, ethanol and sodium acetate trihydrate are then allowed to run in over the course of 10 minutes, whereupon the virtually ethanol-free crystal modification B of the sodium salt of 7-cyanoacetylamino-cephalosporanic acid deposits as a thick crystal paste. Stirring is continued for 2 hours at 20°-25°, and the mixture is then cooled to a temperature of +7° to +10° C and filtered off. The crystals are washed with a total of 4-4.5 liters of ethanol and subsequently dried in vacuo to constant weight, first for several hours without heating and then for 8-10 hours at 40°-42° C. Snow-white, matted acicular crystals are obtained. Yield: 995 g = 93% of theory; $[\alpha]_D^{20}$ = +139.2° (c = 1% in $H_2O$); UV spectrum (in $H_2O$): $\lambda_{max.}$ = 260 nm, $\epsilon$ = 8,750; ethanol content: 0.35%; water content: 0.33%. The X-ray diffraction spectrum corresponds to that of modification B.

EXAMPLE 4

A solution, prepared under nitrogen at 20°-25° C, of 50 g of the sodium salt of 7-cyanoacetylamino-cephalosporanic acid (modification B) in 70 ml of distilled water is filtered under nitrogen and the filter residue is rinsed with 30 ml of distilled water. 300 ml of anhydrous ethanol are added dropwise to the filtrate. In order to complete the crystallisation, stirring is continued for 4 hours, 600 ml of anhydrous ethanol are added dropwise to the crystal paste and the mixture is then cooled to 0° to +3° C. The crystals are filtered off, rinsed with twice 100 ml of anhydrous ethanol and dried for 7 to 8 hours at room temperature in a water pump vacuum and then for 5 to 6 hours at 40° C in a high vacuum. Water content: 0.21%. The X-ray diffraction spectrum corresponds to that of modification B.

EXAMPLE 5

A solution, prepared under nitrogen, of 50 g of the sodium salt of 7-cyanoacetylamino-cephalosporanic acid (modification A) in 70 ml of distilled water is filtered under nitrogen and the filter residue is rinsed with 30 ml of distilled water. 300 ml of anhydrous ethanol are added dropwise to the filtrate. In order to complete the crystallisation, stirring is continued for 4 hours, 600 ml of anhydrous ethanol are added dropwise to the crystal paste and the mixture is then cooled to 0° to +3° C. The crystals are filtered off, rinsed with twice 100 ml of anhydrous ethanol and dried for 7 to 8 hours at room temperature in a water pump vacuum and then for 5 to 6 hours at 40° C in a high vacuum. Water content: 0.28%. The X-ray diffraction spectrum corresponds to that of modification B.

What is claimed is:

1. Process for the manufacture of a virtually solvent free crystal form of the sodium salt of Cephacetril, which has the following X-ray diffraction spectrum:

| Interplanar spacings d in Å | Relative line intensities I |
|---|---|
| 15.2 | m |
| 10.7 | m |
| 7.86 | m |
| 7.60 | w |
| 7.03 | m |
| 5.04 | m-st |
| 4.94 | w |
| 4.65 | st |

| Interplanar spacings d in Å | Relative line intensities I |
|---|---|
| 4.39 | st |
| 4.10 | vst |
| 4.01 | m |
| 3.66 | m |
| 3.59 | vw |
| 3.50 | st |
| 3.36 | vw |
| 3.30 | m |
| 3.18 | m |
| 3.11 | vw |
| 3.04 | w |
| 3.02 | w |
| 2.96 | w |
| 2.88 | w | the relative line intensities indicated having the following meanings: vst = very strong, st = strong, m = medium, w = weak and vw = very weak, wherein the sodium salt of Cephacetril is caused to crystallise from a supersaturated, aqueous-ethanolic solution in which the solvent contains about 4 to 12% of water and at a temperature of between 30° and 0° C.

2. Process according to claim 1, wherein the sodium salt of Cephacetril is caused to crystallise from a supersaturated aqueous-ethanolic solution, wherein the solvent contains about 8% of water.

3. Process according to claim 1, wherein the sodium salt of Cephacetril is caused to crystallise by cooling a concentrated, warm, aqueous-ethanolic solution.

4. Process according to claim 1, wherein the sodium salt of Cephacetril is caused to crystallise by cooling a concentrated aqueous-ethanolic solution from about 20°-30° C to about 0°-10° C.

5. Process according to claim 1, wherein the sodium salt of Cephacetril is caused to crystallise from an aqueous solution by adding ethanol and, if appropriate, cooling to 0° to 10° C.

6. Process according to claim 1, wherein the supersaturated, aqueous-ethanolic solution of the sodium salt of Cephacetril is prepared in situ from Cephacetril and the sodium salt of a weak acid.

7. Process according to claim 1, wherein the sodium salt of Cephacetril is caused to crystallise from a supersaturated solution which is obtained by dissolving Cephacetril in aqueous ethanol which contains about 4 to 12% of water and has a temperature of about 40° to about 60° C, and adding to this solution, preferably after cooling to about 30° C, a concentrated aqueous solution, or preferably a concentrated aqueous-ethanolic solution, of a sodium salt of a weak acid.

8. Process according to claim 1, wherein the sodium salt of Cephacetril is caused to crystallise from a supersaturated solution which is obtained by dissolving Cephacetril in ethanol which contains about 8% of water and has a temperature of about 50° to 52° C, and adding to this solution, after cooling to about 30° C, a concentrated solution of sodium acetate trihydrate in ethanol and water in a weight ratio of 1:1:1.

9. A virtually solvent-free crystal form of the sodium salt of Cephacetril, which, using a Cu:$K_\alpha$ radiation source, has the following X-ray diffraction spectrum:

| Interplanar spacings d in Å | Relative line intensities I |
|---|---|
| 15.2 | m |
| 10.7 | m |
| 7.86 | m |
| 7.60 | w |
| 7.03 | m |
| 5.04 | m-st |
| 4.94 | w |
| 4.65 | st |
| 4.39 | st |
| 4.10 | vst |
| 4.01 | m |
| 3.66 | m |
| 3.59 | vw |
| 3.50 | st |
| 3.36 | vw |
| 3.30 | m |
| 3.18 | m |
| 3.11 | vw |
| 3.04 | w |
| 3.02 | w |
| 2.96 | w |
| 2.88 | w | the relative line intensities indicated having the following meanings: vst = very strong, st = strong, m = medium, w = weak and vw = very weak.

* * * * *